United States Patent [19]

Ziman

[11] 4,326,878
[45] * Apr. 27, 1982

[54] HERBICIDAL AND PLANT-GROWTH-REGULATING 1,2,4-TRISUBSTITUTED-1,2,4-TRIAZOLIDIN-3,5-DITHIONES

[75] Inventor: Stephen D. Ziman, San Francisco, Calif.

[73] Assignee: Chevron Research, San Francisco, Calif.

[*] Notice: The portion of the term of this patent subsequent to Jun. 30, 1998, has been disclaimed.

[21] Appl. No.: 60,310

[22] Filed: Jul. 25, 1979

Related U.S. Application Data

[63] Continuation-in-part of Ser. No. 10,669, Feb. 9, 1979, Pat. No. 4,276,420, which is a continuation-in-part of Ser. No. 909,140, May 24, 1978, abandoned.

[51] Int. Cl.$^3$ ............... A01N 43/64; C07D 249/12
[52] U.S. Cl. ........................... 71/92; 548/264; 71/74; 71/76
[58] Field of Search ............... 71/92, 74, 76; 548/264

[56] References Cited

U.S. PATENT DOCUMENTS

| | | | |
|---|---|---|---|
| 2,944,060 | 7/1960 | Close et al. | 260/308 C |
| 3,184,470 | 5/1965 | Rusenig et al. | 260/308 C |
| 3,621,099 | 11/1971 | Jacobson et al. | 424/269 |
| 3,641,046 | 2/1972 | Gates et al. | 260/308 R |
| 3,663,564 | 5/1972 | Jacobson et al. | 260/308 C |
| 3,767,666 | 10/1973 | Zielinski | 260/308 C |
| 3,922,162 | 11/1975 | Krenzer | 71/92 |
| 3,966,530 | 6/1976 | Cutts et al. | 260/308 C |
| 4,088,767 | 5/1978 | Shigematsu et al. | 548/264 |

FOREIGN PATENT DOCUMENTS 215994 7/1961 Austria.

OTHER PUBLICATIONS

Zinner et al., Archiv. der Phar., vol. 294, (1961), p. 370.

Primary Examiner—Catherine L. Mills
Attorney, Agent, or Firm—J. A. Buchanan, Jr.; T. G. DeJonghe; L. S. Squires

[57] ABSTRACT

1,2,4-Trisubstituted-1,2,4-triazolidin-3,5-dithiones are prepared by the reaction of a 1,2,4-trisubstituted 1,2,4-triazolidin-3-one-5-thione and phosphorous pentasulfide in the liquid phase. The triazolidin-dithione compounds are useful as herbicides and plant-growth regulators.

8 Claims, No Drawings

HERBICIDAL AND PLANT-GROWTH-REGULATING 1,2,4-TRISUBSTITUTED-1,2,4-TRIAZOLIDIN-3,5-DITHIONES

RELATED APPLICATION

This application is a continuation-in-part of my co-pending application Ser. No. 10,669, filed Feb. 9, 1979, now U.S. Pat. No. 4,276,420, which in turn is a continuation-in-part of Ser. No. 909,140, filed May 24, 1978, abandoned, the disclosures of which are incorporated herein by reference.

DESCRIPTION OF THE PRIOR ART 1,2-Dialkyl-1,2,4-triazolidine-3,5-diones(2,3-dialkylbicarbamides) are disclosed in U.S. Pat. No. 2,944,060 and Chem. Abstr. 42 8190 (1948).

4-Butyl-1,2,4-triazolidine-3,5-dione and 4-phenyl-1,2,4-triazolidine-3,5-dione are disclosed by Zinner and Deucker, Archiv. der Phar., 294, 370 (1961).

U.S. Pat. No. 3,555,152 discloses 1-alkyl-1,2,4-triazolidine-3,5-diones (2-alkylbicarbamimides); 1,2-dialkyl-1,2,4-triazolidine-3,5-diones (2,3-dialkylbicarbamimides); and fungicidal 1,2-dialkyl-4-haloalkylthio-1,2,4-triazolidine-3,5-diones [2,3-dialkyl-N-(haloalkylthio)bicarbamimides].

Chemical Abstracts, Vol. 88, 74395w (1978) discloses herbicidal 1,2-disubstituted-3-alkoxycarboimino-4-substituted-s-triazolidine-5-thiones.

U.S. Pat. No. 4,049,820 discloses the use of substituted urazole and thiourazole compounds as fungicidal agents.

DESCRIPTION OF THE INVENTION

The 1,2,4-triazolidin-3,5-dithiones of the invention are represented by Formula (I):

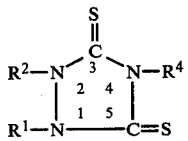

(I)

wherein $R^1$ is alkyl of 1 to 6 carbon atoms, $R^2$ is alkyl of 1 to 6 carbon atoms, phenyl, or phenyl substituted with 1 to 2 of the same or different substituents selected from fluoro, chloro, bromo, iodo, alkyl of 1 to 4 carbon atoms, haloalkyl of 1 to 2 carbon atoms and of 1 to 3 fluoro, chloro, bromo or iodo, alkoxy of 1 to 3 carbon atoms or nitro, alkoxyalkyl of 2 to 6 carbon atoms, alkenyl of 2 to 6 carbon atoms, alkylthioalkyl of 2 to 6 carbon atoms, alkylthio of 1 to 3 carbon atoms, alkynyl of 2 to 6 carbon atoms, cycloalkyl of 3 to 6 carbon atoms, (cycloalkyl)-alkyl of 4 to 8 carbon atoms, or haloalkyl of 1 to 4 carbon atoms and 1 to 9 fluoro, chloro, bromo or iodo, and $R^4$ is alkyl of 1 to 6 carbon atoms, phenyl or phenyl substituted with 1 to 2 of the same or different substituents selected from fluoro, chloro, bromo, iodo, alkyl of 1 to 4 carbon atoms, haloalkyl of 1 to 2 carbon atoms and of 1 to 3 fluoro, chloro, bromo or iodo, alkoxy of 1 to 3 carbon atoms or nitro.

Representative alkyl $R^1$, $R^2$ and $R^4$ groups are methyl, ethyl, propyl, etc.

Representative $R^2$ groups also include vinyl, allyl, methoxymethyl, methylthiomethyl, cyclopropylmethyl, cyclopentylmethyl, cyclopropyl and 2-bromoethyl.

Representative substituted phenyl $R^2$ and $R^4$ groups include 2-fluorophenyl, 2-chlorophenyl, 3-bromophenyl, 2,4-diiodophenyl, 4-chloromethylphenyl, 3-trichloromethylphenyl, 4-methoxyphenyl, 3-nitrophenyl, and 3,5-dinitrophenyl.

Preferably $R^1$ is alkyl of 1 to 3 carbon atoms, especially methyl. Preferably $R^2$ is alkyl of 1 to 3 carbon atoms, alkenyl of 2 to 6 carbon atoms, alkoxyalkyl of 2 to 6 carbon atoms and alkylthioalkyl of 2 to 6 carbon atoms. More preferably, $R^2$ is methyl, ethyl, vinyl, allyl, methoxymethyl or methylthiomethyl. Most preferably $R^2$ is ethyl.

Preferably $R^4$ is phenyl substituted with 1 to 2 fluoro, chloro, bromo or iodo. Most preferably $R^4$ is phenyl substituted with 1 to 2 fluoro or chloro.

The compounds of the invention can be prepared by reacting a semicarbazide (II) and thiophosgene (III) in accordance with reaction (1), followed by treatment with phosphorous pentasulfide by reaction (2), as follows:

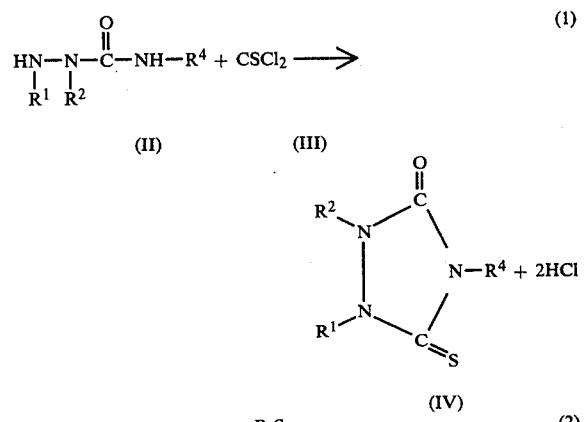

$$IV \xrightarrow[\text{heat}]{P_2S_5} I \quad (2)$$

wherein $R^1$, $R^2$ and $R^4$ have the same significance as previously defined.

Reaction (1) can be conducted by reacting substantially molar amounts of the semicarbazide (II) and thiophosgene (III) in the liquid phase in an inert diluent. Generally, the molar ratios of semicarbazide to thiophosgene vary from about 1.2:1 to 1:1.2, although molar ratios of from about 1.1:1 to 1:1.1 are preferred. Reaction (1) is conducted in the presence of a base to scavenge the hydrogen chloride produced in the reaction. Generally, the molar ratios of base to thiophosgene vary from about 2.2:1 to 2:1. Suitable bases include organic nitrogen bases such as trialkylamines, e.g., triethylamine and tributylamine, and pyridine compounds, e.g., pyridine and 2-methylpyridine. Inorganic bases such as alkali metal carbonates and bicarbonates, e.g., sodium carbonate and potassium bicarbonate, can also be used.

The reaction is conducted in inert organic diluents, e.g., haloalkanes such as dichloromethane and chloroform, aromatic compounds such as benzene, toluene and chlorobenzene, and ethers such as dimethoxyethane, tetrahydrofuran and dioxane. Reaction temperatures vary from about 0° to 150° C., although temperatures of from about 20° C. to 100° C. are preferred. The reaction pressure can be atmospheric, subatmospheric or superatmospheric. However, for convenience of conducting the reaction, the pressure is generally atmospheric. The reaction time will, of course, vary depending upon the particular reactants and the reaction temperature. Generally, the reaction time is from several minutes to 24 hours. The product (I) is generally isolated and purified by conventional procedures, e.g., extraction, chromatography, crystallization, etc.

Reaction (2) may be conducted at reflux temperature in a suitable solvent, such as xylene.

I have found that the more preferable method for preparing the intermediate triazolidin-3-one-5-thiones (IV) is to use monosubstituted hydrazine (IVa) and carbon disulfide as starting materials in accordance with the following scheme:

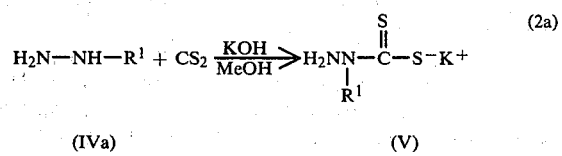

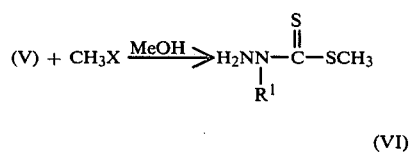

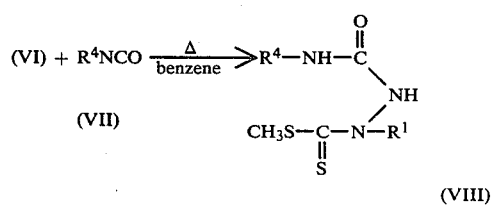

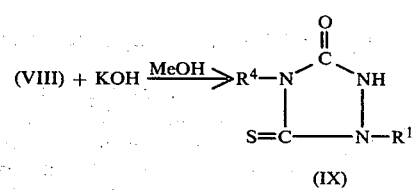

The disubstituted cyclic intermediate (IX) can then be alkylated with $R^2X$ by the following reaction, wherein $R^2$ is defined above and X is halo:

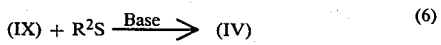

Reactions (2a) through (5) may be conducted in inert organic diluents other than those indicated, e.g., haloalkanes such as dichloromethane and chloroform, aromatic compounds such as benzene, toluene and chlorobenzene, and ethers such as dimethoxyethane, tetrahydrofuran and dioxane. Reaction temperatures for reactions (2a), (3) and (5) are normally room temperature. Reaction (4) may be performed from ambient to 80° C. Reaction (6) is conducted at the reflux temperature of the solvent, preferably DMF. The reaction pressures for reactions (2) through (6) can be atmospheric, subatmospheric or superatmospheric. However, for convenience of conducting the reactions, the pressure is generally atmospheric. Reaction (6) is performed in the presence of a strong base, preferably sodium hydride. The reaction time for each reaction will, of course, vary depending upon the particular reactants and the reaction temperature. Generally, the reaction times vary from several minutes to 24 hours. The product (I) is generally isolated and purified by conventional procedures, e.g., extraction, chromatography, crystallization, etc.

EXAMPLES

Example 1

Preparation of 1,2-dimethyl-4-phenyl-1,2,4-triazolidine-3-one-5-thione

A solution of 4.26 g (0.037 mol) thiophosgene in about 10 ml chloroform was added dropwise to a solution of 6.7 g (0.037 mol) 1,2-dimethyl-4-phenylsemicarbazide and 7.47 g (0.074 mol) triethylamine in 200 ml chloroform. A slightly exothermic reaction ensued. One hour after the addition was completed, the reaction mixture was heated under reflux for about 16 hours, cooled and evaporated under reduced pressure to give an oil residue. The residue was dissolved in dichloromethane, washed with water, dried over magnesium sulfate, filtered and evaporated under reduced pressure to give a red viscous oil. The oil was chromatographed on 200 g of silica gel using dichloromethane as eluant. The major product (4 g) from the chromatography was a semisolid, which on trituration with ether gave the desired product as a light tan solid, m.p. 118°–122° C. Infrared spectrum of the product showed strong carbonyl absorption at 5.8 micron. The product is tabulated in Table I as Compound No. 1.

EXAMPLE 2

Preparation of 1,2-dimethyl-4-(4-chlorophenyl)-1,2,4-triazolidin-3-one-5-thione

A solution of 3.8 g (0.33 mol) thiophosgene in 10 ml chloroform was added dropwise to a stirred solution of 7 g (0.033 mol) 1,2-dimethyl-4-(4-chlorophenyl)-semicarbazide and 6.67 g (0.066 mol) triethylamine in 200 ml chloroform. After completion of the addition, the reaction mixture was heated under reflux for 2 hours and stirred at about 25° C. for 3 days. The reaction mixture was then washed with water, dilute hydrochloric acid solution, dried over magnesium sulfate, filtered and evaporated under reduced pressure to give 10 g of a semi-solid residue. The residue was diluted with 100 ml dichloromethane and filtered. The filtrate was chromatographed on 200 g of silica gel. Elution with 1% methanol in dichloromethane gave the product, 3.9 g, as light tan crystals, m.p. 143°–144° C. Infrared analysis showed strong carbonyl absorption at 5.8 micron. The product is tabulated in Table I as Compound No. 2.

EXAMPLE 3

Preparation of 1-methyl-2-methoxymethyl-4-(4-chlorophenyl)-1,2,4-triazolidin-3-one-5-thione To 1-methyl-4-(4-chlorophenyl)-1,2,4-triazolidin-3-one-5-thione (5 g) in 200 ml dry DMF was added 0.91 g sodium hydride. After stirring for 30 minutes, bromomethyl methyl ether (2.63 g) was added dropwise, then heated to reflux for 30 minutes, and stirred overnight at room temperature. The solvent was stripped and the residue was dissolved in methylene chloride, washed with water, and chromatographed on a silica gel column (200 g) by elution with methylene chloride, followed by 2.5% methanol in methylene chloride. Yield: 4.8 g.

EXAMPLE 4

Preparation of 1-methyl-2-vinyl-4-(4-chlorophenyl)-1,2,4-triazolidin-3-one-5-thione A mixture of 5.9 g of 1-methyl-2-(2-bromoethyl)-4-(4-chlorophenyl)-1,2,4-triazolidin-3-one-5-thione (prepared as in Example 3) and 2.1 g 1,5-diaza-bicyclo[4.3.0]non-5-ene in 100 ml chloroform was heated to reflux for 3 hours and stirred overnight at room temperature. The mixture was washed with water, dried ($MgSO_4$), stripped and chromatographed by high-pressure liquid chromatography. Yield: 2.6 g.

EXAMPLE 5

Preparation of 1-methyl-2-ethyl-4-(4-chlorophenyl)-1,2,4-triazolidin-3,5-dithione To 1-methyl-2-ethyl-4-(4-chlorophenyl)-1,2,4-triazolidin-3-one-5-thione (6.44 g) in 100 ml xylene was added phosphorous pentasulfide (5.3 g) and the mixture was refluxed for three hours. The xylene was stripped off, ethanol was added to the residue and mixture was boiled, filtered. Upon cooling the filtrate 3.7 g of the title product was obtained as a white solid.

The compounds tabulated in Table I were prepared by procedures similar to those of Examples 1–5. The structure of each compound tabulated in Table I was confirmed by nuclear magnetic resonance and/or infrared spectroscopy.

UTILITY

The compounds of the present invention are, in general, herbicidal in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broad-leaved weeds. Some may be selective with respect to the type of application and/or type of weed. The compounds are particularly effective as pre-emergent herbicides against broad-leaved plants.

The compounds, when applied to growing plants above the ground in such an amount that the compounds will not kill beneficial plants, also show efficient plant growth regulating or retarding effects and may be advantageously employed, for example, to prevent or retard the growth of lateral buds in plants and to promote the thinning out of superfluous fruits in various fruit trees.

The compounds can be applied in any of a variety of compositions. In general, the compounds can be extended with a carrier material of the kind used and commonly referred to in the art such as inert solids, water and organic liquids.

The compounds will be included in such compositions in sufficient amount so that they can exert an herbicidal or growth-regulating effect. Usually from about 0.5 to 95% by weight of the compounds are included in such formulations.

Solid compositions can be made with inert powders. The compositions thus can be homogeneous powders that can be used as such, diluted with inert solids to form dusts, or suspended in a suitable liquid medium for spray application. The powders usually comprise the active ingredient admixed with minor amounts of conditioning agents. Natural clays, either absorptive, such as attapulgite, or relatively non-absorptive such as china clays, diatomaceous earth, synthetic fine silica, calcium silicate and other inert solid carriers of the kind conventionally employed in powdered herbicidal compositions can be used. The active ingredient usually makes up from 0.5–90% of these powder compositions. The solids ordinarily should be very finely divided. For conversion of the powders to dusts, talc, pyrophyllite, and the like, are customarily used.

Liquid compositions including the active compounds described above can be prepared by admixing the compound with a suitable liquid diluent medium. Typical of the liquid media commonly employed are methanol, benzene, toluene, and the like. The active ingredient usually makes up from about 0.5 to 50% of these liquid compositions. Some of these compositions are designated to be used as such, and others to be extended with large quantities of water.

Compositions in the form of wettable powders or liquids can also include one or more surface-active agents, such as wetting, dispersing or emulsifying agents. The surface-active agents cause the compositions of wettable powders or liquids to disperse or emulsify easily in water to give aqueous sprays.

The surface-active agents employed can be of the anionic, cationic or nonionic type. They include, for example, sodium long-chain carboxylates, alkyl aryl sulfonates, sodium lauryl sulfate, polyethylene oxides, lignin sulfonates and other surface-active agents.

When used as a pre-emergent treatment, it is desirable to include a fertilizer, an insecticide, a fungicide or another herbicide.

The amount of compound or composition administered will vary with the particular plant part or plant growth medium which is to be contacted, the general location of application—i.e., sheltered areas such as greenhouses, as compared to exposed areas such as fields—as well as the desired type of control. Generally for both pre- and post-emergent herbicidal control, the compounds of the invention are applied at rates of 0.2 to 60 kg/ha, and the preferred rate is in the range 0.5 to 40 kg/ha. For plant growth regulating or retarding activity, it is essential to apply the triazolidine compounds at a concentration not so high as to kill the plants. Therefore, the application rates for plant growth regulating or retarding activity will generally be lower than the rates used for killing the plants. Generally, such rates vary from 0.1 to 5 kg/ha, and preferably from 0.1 to 3 kg/ha.

Herbicidal and plant-growth-regulating tests on representative compounds of the invention were made using the following methods.

PRE-EMERGENT HERBICIDAL TEST

An acetone solution of the test compound was prepared by mixing 375 mg of the compound, 118 mg of a nonionic surfactant and 18 ml of acetone. 10 ml of this solution was added to 40 ml of water to give the test solution.

Seeds of the test vegetation were planted in a pot of soil and the test solution was sprayed uniformly onto the soil surface at a dose of 27.5 micrograms/cm$^2$. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table II.

POST-EMERGENT HERBICIDAL TEST

The test compound was formulated in the same manner as described above for the pre-emergent test. This formulation was uniformly sprayed on 2 similar pots of 24-day-old plants (approximately 15 to 25 plants per pot) at a dose of 27.5 microgram/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear in Table II.

AXILLARY BUD GROWTH INHIBITION OF PINTO BEAN PLANTS

Compound No. 2 was tested to determine its plant-growth-retarding effects on axillary bud growth of pinto beans.

Idaho pinto bean plants (13–16 days old) having mono foliate leaves fully developed and first trifoliates beginning to unfold were used. All growth 5 mm above the monofoliate leaf node was removed with forceps 1 to 4 hours prior to treatment with the test compounds. Four plants were used for each test compound.

A 625-ppm solution of the test compound in a 2% aqueous acetone solution containing a small amount of a non-ionic surfactant was sprayed onto the pinto bean plants until runoff. After drying, the treated plants were transferred to a greenhouse maintained at 20°–23° C. and watered at regular intervals. Twelve days after treatment, the bud growth at the axil of the monofoliate leaf was determined and expressed as percent inhibition of axillary bud growth as compared to untreated check plants. The percent inhibition for Compound No. 2 was 85%.

COTTON DEFOLIATION TEST

Compounds No. 2 and 13 were tested to determine their post-emergent foliar activity for cotton defoliation and/or desiccation.

Cotton plants (26–35 days old) with 4 fully expanded leaves were used. Two days before use, the growth beyond the 4th leaf was removed.

A 5000-ppm solution of the test compound in acetone containing a small amount of a nonionic surfactant was sprayed on two cotton plants until runoff. The treated plants were transferred to a greenhouse maintained at 23°–25° C. The plants were watered from the base 1–2 times per day using an automatic sub-irrigation system. Ten days after treatment the percent defoliation and desiccation was determined (relative to the original number of mature leaves). The results for Compound No. 2 were 75% defoliation and 18% desiccation. Compound 13 exhibited no defoliation and 5% desiccation.

TABLE I

Compounds of the formula

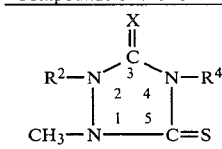

| No. | R$^4$ | R$^2$ | X | m.p., °C. | Elemental Analysis Calculated | | Found | |
|-----|-------|-------|---|-----------|---------|------|-------|------|
| 1 | φ* | CH$_3$ | O | 118–122 | S | 14.3 | S | 14.1 |
| 2 | 4-Cl—φ | CH$_3$ | O | 139–142 | S | 12.5 | S | 12.3 |
|   |        |         |   |         | Cl | 13.9 | Cl | 12.9 |
| 3 | 3,4-Cl$_2$—φ | CH$_3$ | O | 165–167 | S | 11.0 | S | 11.6 |
|   |        |         |   |         | Cl | 24.5 | Cl | 22.7 |
| 4 | 3-CF$_3$—φ | CH$_3$ | O | 107–109 | C | 45.7 | C | 46.3 |
|   |        |         |   |         | H | 3.5 | H | 3.6 |
|   |        |         |   |         | N | 14.5 | N | 14.9 |
| 5 | 4-F—φ | CH$_3$ | O | 178–180 | C | 50.2 | C | 50.8 |
|   |        |         |   |         | H | 4.2 | H | 4.4 |
|   |        |         |   |         | N | 17.6 | N | 17.9 |
| 6 | 3-CF$_3$—4-Cl—φ | CH$_3$ | O | 157–159 | C | 40.7 | C | 40.4 |
|   |        |         |   |         | H | 2.8 | H | 2.8 |
|   |        |         |   |         | N | 13.0 | N | 13.8 |
| 7 | 4-Cl—φ | CH$_2$=CHCH$_2$ | O | 107–108 | N | 14.92 | N | 15.26 |
|   |        |         |   |         | C | 51.15 | C | 51.08 |
|   |        |         |   |         | H | 4.26 | H | 4.37 |
| 8 | 4-Cl—φ | CH$_3$OCH$_2$ | O | 106–108.5 | N | 14.71 | N | 15.05 |
|   |        |         |   |         | C | 46.23 | C | 46.38 |
|   |        |         |   |         | H | 4.20 | H | 4.30 |
| 9 | 4-Cl—φ | CH$_3$SCH$_2$ | O | 93–95 | N | 13.93 | N | 15.38 |
|   |        |         |   |         | C | 43.78 | C | 45.51 |

TABLE I-continued

Compounds of the formula

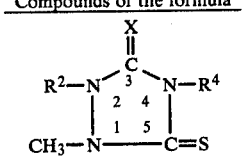

| No. | R⁴ | R² | X | m.p., °C. | Elemental Analysis Calculated | | Found | |
|-----|-----|-----|---|-----------|------|------|------|------|
| 10 | 4-Cl—φ | CH₂ | O | oil | H | 3.98 | H | 4.21 |
|    |        |     |   |     | N | 14.21 | N | 14.58 |
|    |        |     |   |     | C | 52.79 | C | 54.21 |
| 11 | 4-Cl—φ | CH₂=CH | O | 138–140 | H | 4.73 | H | 5.30 |
|    |        |        |   |         | N | 15.70 | N | 15.85 |
|    |        |        |   |         | C | 49.39 | C | 49.19 |
| 12 | 4-Cl—φ | CH₃CH₂ | O | 109–111 | H | 3.74 | H | 4.07 |
|    |        |        |   |         | N | 15.58 | N | 15.94 |
|    |        |        |   |         | C | 48.98 | C | 47.7 |
| 13 | 4-Cl—φ | CH₃CH₂ | S | 219–221 | H | 4.45 | H | 4.80 |
|    |        |        |   |         | C | 46.24 | C | 46.43 |
|    |        |        |   |         | N | 14.71 | N | 14.85 |
|    |        |        |   |         | H | 4.20 | H | 4.35 |

*φ represents phenyl.

TABLE II

Herbicidal Effectiveness
% Control - Pre/Post

| No. | L | M | P | C | W | O |
|-----|---|---|---|---|---|---|
| 1 | 80/45 | 60/0 | 50/0 | 20/0 | 30/0 | 35/0 |
| 2 | 100/85 | 100/70 | 100/88 | 100/20 | 95/50 | 95/20 |
| 3 | 100/78 | 98/35 | 100/20 | 95/20 | 90/20 | 80/0 |
| 4 | 20/20 | 20/30 | 20/20 | 0/0 | 0/0 | 0/0 |
| 5 | 90/35 | 90/20 | 93/40 | 85/0 | 95/0 | 90/0 |
| 6 | 90/0 | 85/0 | 85/0 | 85/0 | 75/0 | 65/0 |
| 7 | 100/95 | 100/100 | 100/95 | 100/93 | 100/97 | 80/80 |
| 8 | 100/100 | 100/100 | 100/100 | 100/75 | 100/95 | 97/75 |
| 9 | 100/80 | 100/77 | 100/87 | 95/50 | 85/55 | —/35 |
| 10 | 100/90 | 100/87 | 97/93 | 98/65 | 98/75 | 90/50 |
| 11 | 100/70 | 100/60 | 100/60 | 100/70 | 100/85 | 93/30 |
| 12 | 100/90 | 100/85 | 100/85 | 100/45 | 100/70 | 85/40 |
| 13 | 100/25 | 100/35 | 100/40 | 100/10 | 93/25 | 80/20 |

L = Lambsquarter (*Chenopodium album*)
M = Mustard (*Brassica arvensis*)
P = Pigweed (*Amaranthus retroflexus*)
C = Crabgrass (*Digitaria sanguinalis*)
W = Watergrass (*Echinochloa crusgalli*)
O = Wild Oats (*Avenua fatua*)

What is claimed is:

1. A compound of the formula

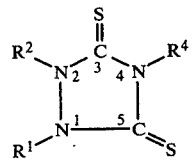

wherein $R^1$ is alkyl of 1 to 3 carbon atoms and $R^2$ is alkyl of 1 to 3 carbon atoms, alkenyl of 2 to 6 carbon atoms, alkoxyalkyl of 2 to 6 carbon atoms and alkylthioalkyl of 2 to 6 carbon atoms, and $R^4$ is p-halophenyl wherein halo is fluoro, chloro, bromo or iodo.

2. The compound of claim 1 wherein $R^4$ is 4-chlorophenyl.

3. The compund of claim 2 wherein $R^1$ is methyl and $R^2$ is ethyl.

4. A method for the control of undesirable vegetation which comprises applying to said vegetation or its growth medium an herbicidally effective amount of the compound of the formula defined in claim 1.

5. The method of claim 4 wherein $R^4$ is 4-chlorophenyl, $R^1$ is methyl and $R^2$ is ethyl.

6. An herbicidal composition comprising a biologically inert carrier and an herbicidally effective amount of the compound of the formula defined in claim 1.

7. A plant-growth-regulating composition comprising a biologically inert carrier and a plant-growth-regulating amount of the compound of the formula defined in claim 1.

8. A method for regulating plant growth which comprises applying to said plants or their growth environment a plant-growth-retarding amount of the compound of the formula defined in claim 1.

* * * * *